United States Patent [19]  [11] 4,004,074
Gerecht et al.  [45] Jan. 18, 1977

[54] HIGHLY SUBSTANTIVE SUNSCREENING AGENTS

[75] Inventors: John Fred Gerecht, Somerville, N.J.; Morton Batlan Epstein, Chicago, Ill.

[73] Assignee: Colgate-Palmolive Company, New York, N.Y.

[22] Filed: Feb. 28, 1973

[21] Appl. No.: 336,839

Related U.S. Application Data

[63] Continuation of Ser. No. 737,822, June 18, 1968, abandoned.

[52] U.S. Cl. .......................... 526/305; 260/79.5 R; 260/79.7; 424/59; 424/69; 424/78; 526/326
[51] Int. Cl.² ............. C08F 218/04; C08F 220/54; C08F 228/02
[58] Field of Search ........ 260/79.5 R, 79.7, 80.3 N, 260/80.81, 78 UA, 85.7, 88.1 PC, 88.1 PN, 78.5 UA; 424/78, 59, 69; 526/305, 326

[56] References Cited

UNITED STATES PATENTS 3,152,181  10/1964  Shapiro et al. .................... 260/564
3,441,589  4/1969  Oswald .............................. 260/455
3,529,055  9/1970  Skoultchi et al. .................. 424/47

OTHER PUBLICATIONS

Geise et al., Journal of the American Pharmaceutical Assoc., vol. 34, pp. 208–212 (1945).
Geise et al., Journal of the American Pharmaceutical Assoc., vol. 39, pp. 30–36 (1950).

Primary Examiner—John Kight, III
Attorney, Agent, or Firm—Herbert S. Sylvester; Murray M. Grill

[57] ABSTRACT

Sunscreening agents having improved adhesion to human skin comprising a polymeric material having a sunscreening group, e.g., a salicylate, aminobenzoate or a para-carboxy succinanilic acid group and having a substrate-binding group, e.g., a thioacetate, mercaptan, guanidyl or biguanidyl group. A representative species is a copolymer of vinylthioacetate and vinyl salicylate.

8 Claims, No Drawings

HIGHLY SUBSTANTIVE SUNSCREENING AGENTS

This is a continuation of application Ser. No. 737,822 filed June 18, 1968 now abandoned.

BACKGROUND OF THE INVENTION

The present invention relates to sunscreening agents having improved adhesion to the skin, and to the preparation of said sunscreening agents.

"Sunscreens", synthetic compounds that absorb strongly in the ultraviolet region of the spectrum, have found wide use as protective agents against sunburn or erythema. Of the many compounds which have been tried over the years (E. G. Klarmann, Am. Perf. and Essential Oil Rev. 58 33-8 126–35 (1949)) derivatives of salicylic acid, p-aminobenzoic acid, 2-hydroxybenzophenone and 2-hydroxyphenylbenzotriazole have emerged as the most desirable "sunscreens" from the practical as well as the theoretical point of view. However, as yet, no product is available which through regular use would impart convenient and constant protection against the damaging effects of ultraviolet radiation.

At least as early as 1946 it was recognized that one of the deficiencies of then existing "sun-tan" lotions was failure to protect because the sunscreen agent was diluted or floated off by perspiration. Resistance to water or sweat can be imparted to a degree by incorporating water repellents or emollients in the formulations. However, for various purposes such as more than occasional use and for incorporation in a variety of products it is advantageous to have, as an active agent or agents in a formulation, materials which not only absorb erythemal radiation but also adhere strongly to the skin.

Many compounds capable of absorbing ultraviolet radiation have been described in the literature and recommended as sunscreening agents. Among those recommended are the following:

| TYPE | SPECIFIC FORM |
|---|---|
| Aminobenzoic acids | o- and p-aminobenzoates and anthranilates |
| Hydroxybenzoic acids | salicylates and tannates |
| Cinnamic acid | menthyl and benzyl esters |
| Coumarins | unbelliferones; quercetin; esculin; daphnin |
| Biphenyls | o- and p-dihydroxybiphenyl disulfonates |
| Naphthols | sulfonates and carboxylates |
| Benzothiazoles | condensations of aromatic aldehydes and aminothiophenol |
| Imidazoles | uric acid and histidine derivative; urocanic acid |
| "Sulfa" drugs | n',n'-Dimethyl-n⁴-sulfanilyl-sulfanilamide; n⁴-sulfanilyl-sulfanilamide |
| Aromatic ketones | benzalacetone; butyl-cinnamyl pyruvate |
| Piperonals | |
| Benzophenones | Highly purified, light yellow, powdered benzophenones, e.g., 2,2'-dihydroxy-4,4'-dimethoxy-benzophenone |
| Hydrocarbons | stilbenes acetanilide Vitamin C |

Most of the foregoing and other materials having the capability of absorbing ultraviolet light have not proved satisfactory for use as sunscreen agents for one or more of the following reasons: coat, safety, discoloration of fabrics, among others. Some are not sufficiently selective between erythemal and tanning radiation. In spite of the deficiencies of the presently recognized sunscreening agents the most widely used at the present time are derivatives of aminobenzoic acid, salicylic acid, and the substituted benzophenones marketed under the tradename, "Uvinul."

SUMMARY OF THE INVENTION

It has been found that sunscreen agents such as those listed hereinbefore can be made substantive by combining one or more sunscreening moieties with one or more molecules of a substantive material to provide polymeric sunscreening material. As used herein the work polymeric includes oligomeric, and the word polymers includes oligomers. Thus, for example, a sunscreening moiety can be combined with a substantive moiety having the capability under ambient conditions to form a disulfide linkage comprising sulfur of the keratin of the skin and sulfur of the substantive moiety of the polymeric sunscreening material. In a similar manner by combining a sunscreening moiety with a guanidyl or biguanide moiety a polymeric sunscreening material is obtained which is strongly substantive to the skin. Accordingly, the present invention provides high substantive polymeric sunscreen agents comprising a sunscreen moiety and at least one substrate-linking moiety selected from the group consisting of thiocarboxylic acids, mercaptans, guanidines, and biguanides. While it is presently preferred to have a plurality of substrate-binding moieties in the sunscreening material, sunscreening material having only one substrate-binding moiety can be used. Accordingly, it is preferred to use polymeric materials although oligomeric analogs can be useful.

Accordingly, it is an object of the present invention to provide highly substantive polymeric sunscreen agents having a plurality of substrate-binding moieties and a plurality of sunscreen moieties.

It is another object of the present invention to provide highly substantive polymeric sunscreen agents having a plurality of substrate-binding moieties capable of forming disulfide which link the substrate and the sunscreen moiety of the polymeric sunscreen agent to the material.

It is a further object of the present invention to provide highly substantive polymeric sunscreen agents having a plurality of substrate-binding moieties comprising guanidyl groups.

The present invention also includes within its scope compounds or materials providing highly substantive polymeric sunscreen agents in which the substrate-binding moiety is a biguanidyl group.

The foregoing and other objects of the present invention will become apparent to those skilled in the art from the following description of highly substantive sunscreening materials.

DESCRIPTION OF THE PREFERRED EMBODIMENTS

As used herein substantive has the usual meaning of attaching directly to the substrate. Substrate includes hair, skin, protein generally, cotton, nylon, and the like.

Guanidyl is RNHC(:NH)NH$_2$
Biguanidyl is RNHC(:NH)NHC(:NH)NH$_2$
Sunscreening moiety — a molecule absorbing light rays in the range of about 2800 Angstroms to about 3200 Angstroms and presently preferred any one of aminobenzoic acids, hydroxybenzoic acids, etc., as listed hereinbefore.

Presently preferred highly substantive sunscreen agents are exemplified by the following:

1. The copolymer of vinylthioacetate and vinyl salicylate.
2. The copolymer of vinylthioacetate and vinyl p-amino benzoate,
3. The copolymer of vinyl mercaptan and maleic anhydride which is further reacted with p-amino benzoic acid to form polymeric succinanilic acid,
4. The copolymer of vinylthioacetate and maleic anhydride further reacted with p-amino benzoic acid,
5. The copolymer of acrylamide of p-amino benzoic acid and vinylthioacetate,
6. The copolymer of allylamide of salicylic acid and vinylthioacetate,
7. The copolymers enumerated hereinbefore in which for the vinylthioacetate or vinyl mercaptan either a vinyl guanidine or a vinyl biguanide is substituted,
8. The polymers of paraguanidyl or biguanidyl styrene,
9. The copolymers of paraguanidyl or biguanidyl styrene and ultraviolet absorbing monomers such as the acrylamide of para-aminobenzoic acid,
10. The copolymers of paraguanidyl or biguanidyl stryene and the allylamide of salicylic acid.

(When necessary the thioacetate groups are hydrolyzed to the free mercaptan).

Those skilled in the art will recognize that the thioacetate or the mercaptan or guanidyl or biguanidyl group or two or more of the aforesaid groups of the exemplary polymers listed above are the substrate-binding groups while the salicylate or aminobenzoate or paracarboxy succinanilic acid groups are the sunscreening moieties.

All these materials bind strongly to the skin whether applied in the form of a solution, a cream, an ointment or an emulsion. When necessary or desirable an auxiliary reducing agent is incorporated which reduces a minor number of the disulfide bonds of the keratin in the skin. Subsequently, the ambient air in an oxidizing reaction brings about reformation of disulfide bonds between the skin and the substrate-binding moiety of the sunscreen material rather than between sulfur atoms of the keratin in the skin.

The testing of compounds for substantivity to skin presents some problems. The most apparent difficulty is the limited availability of human skin. Hence, a material in relatively large supply is a necessary requirement when selecting a material for use as a substrate for controlled evaluation of the substantive as well as the sunscreening composition. Human hair is selected as the test material for the following reasons:

1. It is readily available.
2. It bears a strong relation to the outer layer of skin, the stratum corneum; hydrogen bonds, salt linkages and Van der Waal's forces are considered to play similar roles in both hair and epidermal keratin [W. Montagna and R. A. Ellis, the Biology of Hair Growth, p. 147, Academic Press (1958)].
3. Although its protein structure is not completely known, it is much better characterized chemically than the stratum corneum.

PREPARATION OF HAIR

Approximately 50 gram hanks of untreated De Meo brown hair (from De Meo Brothers, New York City) are cut into ¼ inch-½ inch long clippings with an electric clipper. Each 50 gram hair batch is washed once with 2500 ml. of a 1.0 percent sodium bicarbonate solution by stirring vigorously for about two hours and then leaving it soak overnight. The sodium bicarbonate wash is then decanted and the hair given six consecutive rinses with 2500 ml. portions of deionized water by stirring vigorously for ten minutes, settling for fifteen to twenty minutes and decanting. The sixth water rinse gives 97.5–99 percent light transmission in the 280–320 mu range determined with a Beckman DU quartz spectrophotometer. After decantation of the sixth water rinse, the hair is transferred to a Buchner funnel, broken up into small clumps or mats, and allowed to drain overnight. The bulk of the remaining surface water is removed by pressing the hair mats between paper towels. The last traces of surface water are removed mechanically by breaking down the hair mats into the individual fibers and blotting dry between sheets of filter paper. The hair is then transferred to a 66 percent humidity chamber, over saturated sodium nitrite solution, and conditioned for a minimum period of one week after which it is stored in a screw-capped glass jar until used.

METHOD OF MEASUREMENT

The standard procedure is to soak one gram samples of hair clippings (conditioned as described above) in a 10 ml. portion of a solution of the substantive agent in buffer and in a 10 ml. portion of the corresponding buffer (blank) for a period of exactly 1 hour. The solution and the buffer are then pipetted off from the hair samples and diluted with the original buffer. The solution is diluted to an appropriate concentration for ultraviolet light (UV) absorption measurement and the buffer (blank) is diluted in the same proportion as the solution. UV absorption measurements are run on the diluted solutions and on an equivalent dilution of the original solution of substantive agent with the buffer using a Cary automatic recording spectrophotometer in the 250–350 mu range.

The Cary UV absorption apparatus continuously records the absorbance (A) of the solution, which is directly proportional to the amount of UV absorbing material in the solution. Pickup of the substantive agent by the hair lowers the concentration of material in the solution resulting in a proportionate decrease in the absorbance. The amount of substantive material picked up by the hair as calculated from the decrease in absorbance (at peak absorption) resulting from contact with the hair corrected by the increase in absorbance of the corresponding buffer solution (blank) due to contact with the hair for the same length of time clearly establishes the substantivity of the polymers described herein.

As noted hereinbefore the presently preferred highly substantive sunscreen agents are polymers or copolymers. That is to say the words polymer and copolymer include high molecular weight and low molecular weight materials in which the degree of polymerization is in the range of ten to several thousand, e.g., five thousand. In some instances it is preferred to apply the highly substantive polymeric suncsreen agents as aqueous solutions thereof. Thus, a contradiction might appear to be present in stating that a water-soluble material is water insoluble. This apparent contradiction disappears when it is realized that a chemical reaction takes place when the highly substantive polymeric sunscreen material contacts the substrate. The water-soluble sunscreen material is converted into a relatively water-insoluble material.

For use as an aqueous solution it may be desirable in some instances to adjust the solubility in water of the polymeric sunscreening agent to enable one to prepare more concentrated solutions for use. The solubility in water of the polymeric sunscreen agents can be adjusted by including among the monomers from which the polymeric sunscreen agent is produced one or more monomeric substances which, either because of the hydrocarbon content thereof reduces the solubility of the polymer in water, or because of the polar character thereof increases the solubility of the polymer in water. Thus, for example, to increase the solubility in water of any of the polymers and copolymers mentioned hereinbefore one or more monomeric methylolamides can be included in the mixture of monomers from which the polymer or copolymer is produced.

In some instances it is desirable to introduce a small amount of a cross-linking agent into the monomeric mixture to increase the overall molecular weight of the copolymer. Thus, for example, in the preparation of the copolymer of Example 5 of the foregoing list of exemplary highly substantive suncsreen agents, divinylbenzene can be included in the reaction mixture to increase the molecular weight of the copolymer. In this manner the net substantivity to the substrate can be increased by incorporating a larger number of substantive groups within the polymer molecule or the solubility of the polymeric material can be adjusted.

Exemplary of the preparation of polymers highly substantive to the substrate, for example human skin, is the copolymer of vinylthioacetate and p-allylaminobenzoic acid. Equimolar portions of the monomers vinylthioacetate and p-allylaminobenzoic acid are mixed and held at about 80° C. (176° F.) with about 0.5 percent of azobisisobutyronitrile for about 24 hours. The resulting copolymer is then treated with an excess of aqueous alkali under an inert atmosphere, e.g., nitrogen, to saponify the thioacetate groups to mercaptan groups. The hydrolyzed copolymer, now having the sulfur in mercaptan form, is isolated and recovered by acidifying the reaction mixture with an acid such as hydrochloric acid to precipitate the copolymer. The precipitate is separated from the acidified reaction mixture in any suitable manner, as by filtration. Satisfactory results are also obtained when the ratio of monomers is varied from 90 mols of the thioacetate and 10 mols of the p-allylaminobenzoic acid to 10 mols of the thioacetate and 90 mols of the p-allylaminobenzoic acid.

Polymeric material having a substantive moiety characterized by the guanidyl group can be prepared as follows. The copolymer of p-guanidylstyrene and N-allylsalicylamide is prepared by dissolving equimolar portions of these monomers in about a tenfold quantity of benzene. The benzene solution after the additon of about one percent, based upon the weight of the monomers, of benzoyl peroxide is held at about 60° C. (140° F.) for about 24 hours. The polymeric material is isolated by admixing the reaction mixture very slowly with an excess of methanol. For example, the reaction mixture is dripped into about 100 volumes of methanol. The copolymer precipitate in methanol is filtered and the copolymer recovered.

What is claimed is:

1. A substantive polymeric sunscreening agent consisting essentially of a copolymer of at least one monomeric, substrate binding moiety selected from the group consisting of, vinyl mercaptan, vinyl guanidine, vinyl biguanidine, guanidyl styrene, and biguanidyl styrene, and at least one monomeric sunscreening moiety selected from the group consisting of vinyl or allyl salicylate, vinyl or allyl p-amino-benzoate, allyl amide of p-amino benzoic acid, allyl amide of salicylic acid, and p-allylamino benzoic acid.

2. A substantive polymeric sunscreening agent according to claim 1 wherein the monomeric substrate binding moiety is vinyl mercaptan.

3. A substantive polymeric sunscreening agent according to claim 1 wherein the monomeric substrate binding moiety is guanidyl styrene or biguanidyl styrene.

4. A substantive polymeric sunscreen agent according to claim 1 wherein said agent is a copolymer of p-guanidylstyrene and N-allylamide of salicylic acid.

5. A substantive polymeric sunscreen agent according to claim 1 wherein said agent is a copolymer of vinylmercaptan and N-allylamide of salicylic acid.

6. A substantive polymeric sunscreen agent according to claim 1 wherein said agent is a copolymer of vinylmercaptan and a monomer selected from the group consisting of vinyl and allyl esters of p-amino benzoic acid and salicylic acid.

7. A substantive polymeric sunscreen agent according to claim 1 wherein said sunscreening moiety is provided by a monomer selected from the group consisting of allylamides of p-amino benzoic acid and salicylic acid.

8. A substantive polymeric sunscreen agent according to claim 1 wherein said sunscreening moiety is provided by p-allylamino benzoic acid.

* * * * *